United States Patent [19]

Pinamonti et al.

[11] 4,059,698

[45] Nov. 22, 1977

[54] PESTICIDAL COMPOSITIONS SUITABLE FOR SPREADING FROM AIRCRAFT

[75] Inventors: Franco Pinamonti; Sergio Maccone, both of Milan, Italy

[73] Assignee: Montecatini Edison S.p.A., Milan, Italy

[21] Appl. No.: 447,011

[22] Filed: Feb. 28, 1974

Related U.S. Application Data

[63] Continuation of Ser. No. 798,782, Feb. 12, 1969, abandoned.

[30] Foreign Application Priority Data

Feb. 14, 1968 Italy .................................. 12725/68

[51] Int. Cl.$^2$ ............................................. A01N 9/36
[52] U.S. Cl. .................................... 424/211; 424/173
[58] Field of Search ................................ 424/173, 211

[56] References Cited

U.S. PATENT DOCUMENTS 3,197,362 7/1965 Pinamonti et al. ................... 424/211

OTHER PUBLICATIONS

Pinamonti et al., Chem. Abst. vol. 72 (1970) 65893Z.

*Primary Examiner*—Allen J. Robinson
*Attorney, Agent, or Firm*—Herbert L. Lerner

[57] ABSTRACT

The invention concerns new liquid pesticide compositions with two or three components and which have as an active substance the monomethylamide of the O,O-dimethyldithiophosphorylacetic acid. These compositions are particularly well suited for being spread from aircraft.

4 Claims, No Drawings

PESTICIDAL COMPOSITIONS SUITABLE FOR SPREADING FROM AIRCRAFT

This is a continuation of application Ser. No. 798,782, filed Feb. 12, 1969, now abandoned.

The present invention concerns new pesticide compositions and their use. More particularly, it has as its object new liquid pesticide compositions with two or three components and which have as an active substance the monomethylamide of the O,O-dimethyldithiophosphorylacetic acid. These compositions are particularly well suited for being spread from aircraft.

It is known that for the use of pesticides aircraft the trend today is towards liquid formulations because powdery formulations have the drawback of being carried by winds into areas adjacent to those intended to be treated, with the consequential loss of product or with damage to cultivation and to humans. The use of formulations in aqueous emulsions, in most cases, is also unsuited because of the too rapid evaporation of the water during the dropping of the dispersed phase. Furthermore, the use of emulsions after all has the same drawbacks as powders, because conditions which act negatively on the emulsion stability may easily arise.

The above-mentioned drawbacks can obviously be avoided by using real and proper solutions of active principles, or mixtures which behave as such, in solvents suited for the specific purpose taken into consideration. These solvents will have to be substantially characterized by a low volatility, by a not too excessive inflammability and by a low cost. Substances with such characteristics are easily found among aromatic hydrocarbons or mixtures of aromatic and aliphatic hydrocarbons. The formulation problem suggested is obviously easily solved when substances soluble in such solvents are involved. It is another story, however, when the products used are not soluble or hardly soluble in such solvents. This is the case of the N-monomethylamide of O,O-dimethyldithiophosphorylacetic acid, commercially known under the name of "Rogor" or "Dimethoate".

We have now found that mixtures of Rogor with phenol or cresols or xylenols in suitable percentages (which will be specified hereinbelow and which behave as real and proper solutions stable at even 0° C and less than 0° C) may be conveniently employed for this purpose. We have further found that these compositions may be diluted by solvents of the type suited for being spread from aircraft, with the mixtures obtained therefrom behaving as real and proper solutions.

More particularly, the solvents used for the purpose must preferably display a flammability point above 45° C and an aromatic hydrocarbons content between 65 and 100% with a distillation starting point, at atmospheric pressure, of more than 150° C. Usable as solvents according to this invention are, for instance (without any limiting character):

an aromatic solvent at 99.5%, with a flammability point equal to 63° C, starting point of distillation = 179° C;

an aromatic solvent at 85%, with a flammability point = 58° C and a starting point for distillation = 158° C;

an aromatic solvent at 65%, with a flammability point = 56° C and a starting point for the distillation = 161° C.

The solubility of Rogor in these solvents is about less than 1% at 0° C and less than 3% at 15° C. Now, by mixing the active substance with phenolic type substances, such as those previously indicated, it is possible to obtain compositions that will be stable even at 0° C and will contain from 2 to 70% of the active principle.

Thus, our invention has as an object providing pesticidal compositions having two or three components, particularly well suited for being spread from aircraft, based on N-monomethylamide of O,O-dimethyldithiophosphorylacetic acid, characterized in that they contain in a two-component system, besides Rogor, 15% to 75%, but preferably from 22 to 50%, of phenol, 20% to 96%, but preferably from 35 to 60%, of cresols, 25% to 96%, but preferably from 40 to 60%, of xylenols, alone or in admixture with each other;

while in a three-component system they contain:

at least 2% of N-monomethylamide of the O,O-dimethyldithiophosphorylacetic acid, 0.5% to 75%, but preferably from 0.5 to 50%, of phenol, 0.5% to 96%, but preferably from 0.5 to 50%, of cresols, 0.5% to 96%, but preferably from 0.5 to 50%, of xylenols, taken alone or in admixture with each other, the rest being constituted by an aromatic solvent containing from 0 to 35% by weight of aliphatic hydrocarbons, with a flammability point above 45° C and with a distillation starting point at atmospheric pressure of more than 150° C. The percentage of the hydrocarbon is chosen in such a way as to hinder the separation of the phase in the composition. The preferred values refer to the compositions which are stable at 0° C.

These compositions are particularly well suited, as already said, for being spread from aircraft, but they may also be used conveniently on the ground by means of suitable nebulizing equipment. From the above it should appear as quite evident that our invention puts at the disposal of the users such a wide variety of compositions as to meet all requirements.

As a matter of fact, depending on the necessity related to the type of cultivation, to the degree of infestation and to the type of parasites, preference will be given, for low-volume spraying, to the composition which contains the active substance at the best suited concentration. At any rate, the compositions may already be ready for use without the necessity of diluting them with water, which fact, in places particularly wanting of water resources, may be of very great advantage.

The preparation of such compositions is extremely simple, since it is sufficient to mix the components together without following and pre-established order. The dissolution also takes place in the cold, but is accelerated by a little heating.

The ratio Rogor/phenolic substances, in order to obtain these compositions, varies, depending on the desired stability and on the temperature at which these compositions are intended to be used. Thus, for instance, a composition containing 70% Rogor and 30% phenol will be stable at 0° C. A composition containing 78% Rogor and 22phenol, will be stable at 15° C. In order to obtain solutions, with a not too high contents in active principle, it will be sufficient to add small quantites of phenols, cresols, xylenols and the like. For instance, for a solution at 10% of Rogor, the presence of 5% of phenol is sufficient, the rest being constituted by an aromatic solvent. Still less phenol or phenolic-like substance is required for solutions with a lower contents in active principle.

In order to obtain solutions with a higher contents, it is necessary to increase the quantity of the phenolic type substances. For instance, a solution of 40% Rogor will have to contain 16% phenol or 19% cresols or 23% xylenols, the rest being constituted by an aromatic solvent. At the limit, a solution at a 70% concentration contains 70% Rogor and 30% phenol.

These compositions are stable at 0° C. Compositions stable, for instance, at 15° C require a lower quantity of phenolic type substances. Thus, for instance, a composition at 40% of Rogor, will require 9% of phenol or 11% of cresols or 13% of xylenols, the rest being constituted by aromatic solvent.

The composition of the mixtures varies according to the contents in aliphatic hydrocarbons in the solvent. In has been found that with the increase of the contents in aliphatic hydrocarbons, the contents in phenolic substances must be increased. Thus, for instance, with a solvent at 65% of aromatic substance, in order to get a solution at 10% of Rogor stable at 0° C, it is necessary to add 26% of phenol.

This is a technique of extreme simplicity. It is quite evident that an expert of average skill will not meet any difficulty in preparing the compositions according to the invention.

It is not necessary to use pure phenol, cresols and xylenols. In the case of cresols and xylenols, mixtures of the isomers or mixtures of substances of the phenolic type may be used.

In order to more clearly illustrate the present invention, a series of examples of compositions suited for being spread from aircraft will be given in tabular form, it being understood that these examples shall in no way be taken as limitative of this invention.

TABLE

| Example No. | Rogor % | Compounds Phenol % | Cresols % | Xylenols % | Solvent at 99.5% of aromatic % | Solvent at 85% of aromatic % | Solvent at 65% of aromatic % |
|---|---|---|---|---|---|---|---|
| 1 | 10 | 5 | — | — | 85 | — | — |
| 2 | 10 | 26 | — | — | — | — | 64 |
| 3 | 40 | 16 | — | — | 44 | — | — |
| 4 | 40 | 34 | — | — | — | 26 | — |
| 5 | 10 | — | 6 | — | 84 | — | — |
| 6 | 10 | — | 20 | — | — | — | 70 |
| 7 | 40 | — | 19 | — | 41 | — | — |
| 8 | 40 | — | 30 | — | — | 30 | — |
| 9 | 10 | — | — | 6 | 84 | — | — |
| 10 | 10 | — | — | 15 | — | — | 75 |
| 11 | 40 | — | — | 23 | 37 | — | — |
| 12 | 40 | — | — | 25 | — | 35 | — |
| 13 | 10 | 2.5 | 3 | — | 84.5 | — | — |
| 14 | 10 | 2.5 | — | 3 | 84.5 | — | — |
| 15 | 10 | — | 3 | 3 | 84 | — | — |
| 16 | 70 | 30 | — | — | — | — | — |
| 17 | 65 | — | 35 | — | — | — | — |
| 18 | 60 | — | — | 40 | — | — | — |
| 19 | 65 | 15 | 20 | — | — | — | — |
| 20 | 60 | 15 | — | 25 | — | — | — |
| 21 | 60 | — | 20 | 20 | — | — | — |
| 22 | 10 | 3.5 | — | — | 86.5 | — | — |
| 23 | 40 | 9 | — | — | 51 | — | — |
| 24 | 10 | — | 4 | — | 86 | — | — |
| 25 | 40 | — | 11 | — | 49 | — | — |
| 26 | 10 | — | — | 5 | 85 | — | — |
| 27 | 40 | — | — | 13 | 47 | — | — |
| 28 | 78 | 22 | — | — | — | — | — |
| 29 | 72 | — | 28 | — | — | — | — |
| 30 | 66 | — | — | 34 | — | — | — |
| 31 | 10 | 2 | 2.5 | 2.5 | 83 | — | — |

We claim:

1. Liquid pesticide composition suitable for being spread from aircraft containing a solution of N-monomethylamide of the O,O-dimethyldithiophosphoryl acetic acid in a mixture of a phenolic material selected from the group consisting of phenol, cresols, xylenols and mixtures thereof, and a mixture of aromatic and aliphatic hydrocarbons having a distillation starting point at atmospheric pressure above 150° C, a flammability point above 45° C, an aliphatic hydrocarbon content of from 0 to 35% and an aromatic hydrocarbon content of 65 to 100%, said solution being composed of at least 2% N-monomethylamide of the O,O dimethyldithiophosphoryl acetic acid, 0.5–50% of said phenolic material, and the remainder said mixture of aromatic and aliphatic hydrocarbons, said composition being stable at 0° C.

2. Liquid pesticide composition of claim 1 wherein said mixture of aliphatic and aromatic hydrocarbons has an aromatic content of about 65%, a flammability point of about 56° C, and a distillation starting point of about 161° C.

3. Liquid pesticide composition of claim 1 wherein said mixture of aliphatic and aromatic hydrocarbons has an aromatic content of about 85%, a flammability point of about 58° C, and a distillation starting point of about 158° C.

4. Liquid pesticide composition of claim 1 wherein said mixture of aliphatic and aromatic hydrocarbons has an aromatic content of about 99.5%, a flammability point of about 63° C, and a distillation starting point of about 179° C.

* * * * *